(12) United States Patent
Rose et al.

(10) Patent No.: US 6,635,241 B1
(45) Date of Patent: Oct. 21, 2003

(54) AMINOPHENOL DERIVATIVES AND THEIR USE IN OXIDATIVE HAIR DYES

(75) Inventors: David Rose, Hilden (DE); Horst Hoeffkes, Duesseldorf (DE); Bernd Meinigke, Leverkusen (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/125,844

(22) PCT Filed: Feb. 19, 1997

(86) PCT No.: PCT/EP97/00767

§ 371 (c)(1),
(2), (4) Date: Jan. 22, 1999

(87) PCT Pub. No.: WO97/31886

PCT Pub. Date: Sep. 4, 1997

(30) Foreign Application Priority Data

Feb. 29, 1996 (DE) .......................................... 196 07 751

(51) Int. Cl.[7] .............................. A01K 7/06; A01K 7/04
(52) U.S. Cl. .......................................... 424/70.6; 424/61
(58) Field of Search .................................. 424/70.6, 61

(56) References Cited

U.S. PATENT DOCUMENTS

| | | | |
|---|---|---|---|
| 3,574,749 A | | 4/1971 | Howe et al. |
| 3,862,976 A | * | 1/1975 | Booth |
| 4,865,774 A | | 9/1989 | Fabry et al. |
| 4,931,218 A | | 6/1990 | Schenker et al. |
| 5,084,067 A | | 1/1992 | Junino et al. |
| 5,294,726 A | | 3/1994 | Behler et al. |
| 5,364,413 A | | 11/1994 | Junino et al. |
| 5,503,640 A | | 4/1996 | Junino et al. |

FOREIGN PATENT DOCUMENTS

| | | |
|---|---|---|
| DE | 82445 | 7/1894 |
| DE | 25 18 393 | 11/1976 |
| DE | 37 23 354 | 1/1989 |
| DE | 37 25 030 | 2/1989 |
| DE | 39 26 344 | 2/1991 |
| DE | 43 44 551 | 6/1995 |
| EP | 0 011 843 | 6/1980 |
| EP | 0 331 144 | 9/1989 |
| FR | 1 543 690 | 9/1968 |
| WO | WO92/13824 | 8/1992 |

OTHER PUBLICATIONS

Hershfield, R. et al., The Lactonization of Ring–Substituted Coumarinic Acids, Structural Effects on the Partitioning of Tetrahedral Intermediates in Esterification, J. Amer. Chem. Soc. 95:22, pp. 7359–7369 (Oct. 1973).

Hurd, C. et al., "The Behavior of Allyl Derivatives of Catechol and Resorcinol Toward Heat," J. Amer. Chem. Soc., vol. 52, pp. 1700–1706 (Apr. 1930).

Parsons, D., Synthesis of Bridged Macrocyclic Polyethers of High Complexing Ability with Group 1a Salts, J. Amer. Chem. Soc., Perkin Trans I, pp. 451–455 (1978).

J. Org. Chem., vol. 48, No. 25, p. 4867, (1983).

J Amer. Chem. Soc., vol. 99, No. 8, p. 2568 (Apr. 1977).

Oepen, G. et al. "Nichtcyclische Neutralliganden mit Phenol–Endgruppen," Liebigs Ann. Chem., pp. 1592–1597, Verlag Chemie, (1978).

Ekstroem, G. et al., "Diphenylmethane Derivatives with Antibacterial Effect, Especially Against Myobacterium Tuberculosis," Chemical Abstracts, vol. 51, No. 12, Abstract No. 8799a, Columbus, OH (Jun. 25, 1957).

Derwent WPI database, Accession No. 1980–41886C [24], abstract of EP 0 011 843 (1980).

Derwent WPI database, Accession No. 1992–269752 [33], abstract of WO 92/13824, (1992).

Derwent WPI database, Accession No. 1976–85191X[46], abstract of DE 2518393, (1976).

Derwent WPI database, Accession No. 1995–283483[37], abstract of DE 4344551, (1995).

EU Inventory of Cosmetic Ingredients, Colipa, Mar. 1996 – on diskette.

* cited by examiner

Primary Examiner—Paul J. Killos
(74) Attorney, Agent, or Firm—Stephen D. Harper; Gregory M. Hill; Glenn E. J. Murphy

(57) ABSTRACT

A method of coloring keratinous fibers comprising contacting the fiber with and effective amount of a primary intermediate general formula (I) or water-soluble salts thereof in which one of the two groups $R^1$ and $R^2$ is hydrogen and the other is hydrogen, chlorine or fluorine; one of the two groups $R^3$ and $R^4$ is hydrogen, a $C_{1-4}$-alkoxy group, a $C_{1-4}$-alkyl group, a $C_{1-4}$-hydroxyalkyl group, preferably with a terminal hydroxy group or halogen and the other is one of the groups: —O—$CH_2$—CH=$CH_2$, —CH=CH—COOX in which X is hydrogen or a physiologically tolerable inorganic or organic cation and, in the case when the group concerned is $R^3$, the group (a) and, in the case when the group concerned is $R^4$, (b), in which —A— in each case is one of the groups —$(CH_2)_x$— in which x=1 to 4, —O—$(CH_2)_y$—O— in which y=1 to 4, —O—$(C_nH_{2n-z}(OH)_z)$—O— in which n=1 to 10 and z=1 or, when n is greater than or equal to 3, z=2, —O—$(C_2H_4$—O$)_u$— in which u=1 to 4 and —O—$(C_3H_6$—O$)_v$— in which v is 1 to 4 and oxidizing the primary intermediate to color the fiber. Brilliant hues with a high degree of fastness are obtained with the usual coupling agents, particularly when dyeing hair.

31 Claims, No Drawings

AMINOPHENOL DERIVATIVES AND THEIR USE IN OXIDATIVE HAIR DYES

CROSS REFERENCE TO RELATED APPLICATIONS

This application is a national stage application under 35 U.S.C. § 371 of international application PCT/EP97/00767 filed on Feb. 19, 1997, the international application not being published in English.

BACKGROUND OF THE INVENTION

This invention relates to new aminophenol derivatives, to their use for coloring keratin fibers and to colorants containing these compounds.

DESCRIPTION OF THE INVENTION

By virtue of their intensive colors and good fastness properties, so-called oxidation colorants play a prominent role in the coloring of keratin fibers, particularly human hair. Oxidation colorants normally contain oxidation dye precursors, so-called primary intermediates and secondary intermediates. The primary intermediates form the actual dyes with one another or by coupling with one or more secondary intermediates in the presence of oxidizing agents or atmospheric oxygen.

Good oxidation dye precursors are expected to satisfy above all the following requirements: they must form the required color tones with sufficient intensity and fastness during the oxidative coupling reaction. In addition, they must be readily absorbed onto the fibers with no significant differences—particularly in the case of human hair—between damaged and freshly regrown hair (levelling behavior). They must be resistant to light, heat and the effect of chemical reducing agents, for example permanent wave lotions. Finally, if they are used to color hair, they should not overly stain the scalp and, above all, should be toxicologically and dermatologically safe.

The primary intermediates normally used are primary aromatic amines containing another free or substituted hydroxy or amino group in the para or ortho position, diaminopyridine derivatives, heterocyclic hydrazones, 4-aminopyrazolone derivatives and 2,4,5,6-tetraaminopyridine and derivatives thereof.

Special representatives are, for example, p-phenylenediamine, p-toluylenediamine, 2,4,5,6-tetraaminopyrimidine. p-aminophenol, N,N-bis-(2-hydroxyethyl)-p-phenylenediamine, 2-(2,5-diaminophenyl)ethanol, 2-(2,5-diaminophenoxy)-ethanol, 1-phenyl-3-carboxyamido-4-amino-5-pyrazolone, 4-amino-3-methylphenol, 2-aminomethyl-4-aminophenol, 2-hydroxy-4,5,6-triaminopyrimidine, 2,4-dihydroxy-5,6-diaminopyrimidine and 2,5,6-triamino-hydroxypyrimidine.

The secondary intermediates used are generally m-phenylenediamine derivatives, naphthols, resorcinols and resorcinol derivatives, pyrazolones and m-aminophenols. Particularly suitable secondary intermediates are α-naphthol, 1,5-, 2,7- and 1,7-dihydroxynaphthalene, 5-amino-2-methylphenol, m-aminophenol, resorcinol, resorcinol monomethyl ether, m-phenylenedi-amine, 1-phenyl-3-methyl-5-pyrazolone, 2,4-dichloro-3-aminophenol, 1,3-bis-(2,4-diaminophenoxy)-propane, 2-chlororesorcinol, 4-chlororesorcinol, 2-chloro-6-methyl-3-aminophenol, 2-amino-4-hydroxypyridine, 2-methyl resorcinol and 5-methyl resorcinol.

So far as other typical dye components are concerned, reference is expressly made to the Colipa list published by the Industrieverband Körperpflege und Waschmittel, Frankfurt.

Generally speaking, a natural-looking hair color cannot be obtained with a primary intermediate alone or with a special combination of primary and secondary intermediates. In practice, therefore, combinations of various primary intermediates and secondary intermediates are normally used. Because of this, there is a constant demand for new improved dye components.

Accordingly, the problem addressed by the present invention was to provide new primary intermediates which would satisfy the requirements oxidation dye precursors are expected to meet to a particular degree.

It has now been found that certain hitherto unknown aminophenol derivatives satisfy the requirements primary intermediates are expected to meet to a particularly high degree. Thus, brilliant color tones extremely resistant to light and washing are obtained using these primary intermediates with most of the known secondary intermediates. In addition, the colors obtained are distinguished by extreme fastness to cold waving and thermal stability and by excellent levelling.

In a first embodiment, therefore, the present invention relates to aminophenol derivatives corresponding to general formula (1):

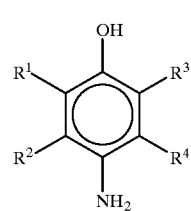

(I)

in which one of the two substituents $R^1$ and $R^2$ is hydrogen and the other substituent is hydrogen, chlorine or fluorine and one of the two substituents $R^3$ and $R^4$ is hydrogen, a $C_{1-4}$ alkyl group, a $C_{1-4}$ alkoxy group a $C_{1-4}$ hydroxyalkyl group, preferably with a terminal hydroxy group, or halogen and the other substituent is one of the following groups:

—O—$CH_2$—CH=$CH_2$,

—CH=CH—COOX, where X is hydrogen or a physiologically compatible inorganic or organic cation, and, in the case of the substituent $R^3$, a group corresponding to the following formula:

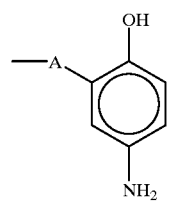

and, in the case of the substituent $R^4$, a group corresponding to the following formula:

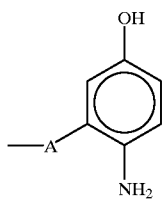

where -A- stands for one of the following groups:

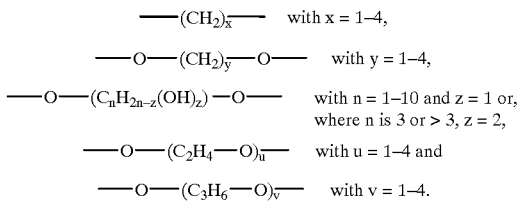

These compounds may be prepared by known organic synthesis methods. So far as the details are concerned, reference is expressly made to the synthesis examples set out in detail in the Examples section.

Since all the compounds according to the invention are amino compounds, the known acid addition salts can be prepared from them by standard methods. Accordingly, all the disclosures of the present specification and, accordingly, the statement of claim relate both to the aminophenol derivatives (I) present in free form and to their water-soluble physiologically compatible salts. Examples of such salts are the hydrochlorides, hydrobromides, sulfates, phosphates, acetates, propionates, citrates and lactates.

The aminophenol derivatives of formula (I), where both $R^1$ and $R^2$ represent hydrogen, have proved to be particularly suitable for the purposes of the invention.

Compounds of formula (I), where one of the two substituents $R^3$ or $R^4$ is hydrogen, are also preferred for the purposes of the invention.

Among the compounds of formula (I) derived from cinnamic acid, the free acids, i.e. X=H, are preferred. However, the alkali metal, alkaline earth metal, aluminium, ammonium and mono-, di- and tri-$C_{1-4}$-hydroxyalkyl ammonium salts may also be used for the purposes of the invention.

Finally, among the compounds representing hydroxyalkyl diethers, those in which R is a number of 1 to 6 and which contain a hydroxy group at the aliphatic chain, i.e. z=1, are preferred.

In the context of the invention as a whole, particularly suitable compounds are
bis-(5-amino-2-hydroxyphenyl)-methane,
3-hydroxy-6-aminoallyloxybenzene,
2-hydroxy-5-aminoallyloxybenzene,
5-amino-2-hydroxycinnamic acid,
bis-[2-(2-hydroxy-5-aminophenoxy)-ethyl]-ether,
1,8-bis-[2-hydroxy-5-aminophenoxy]-3,6-dioxaoctane,
1,3-bis-(2-hydroxy-5-aminophenoxy)-propane and
1,3-bis-(2-hydroxy-5-aminophenoxy)-propan-2-ol.

In a second embodiment, the present invention relates to the use of the aminophenol derivatives mentioned above as primary intermediates in oxidation hair colorants.

Finally, in a third embodiment, the present invention relates to oxidation colorants for coloring keratin fibers containing secondary intermediates and primary intermediates in a water-containing carrier, characterized in that they contain one of the above-mentioned aminophenol derivatives as primary intermediate.

Keratin fibers in the context of the invention include pelts, wool, feathers and, in particular, human hair. Although the oxidation colorants according to the invention are particularly suitable for coloring keratin fibers, there is in principle nothing to prevent them from being used in other fields, particularly in color photography.

The oxidation colorants according to the invention contain the primary intermediates according to the invention and, if desired, may contain other primary intermediates and secondary intermediates. So far as the other primary and secondary intermediates are concerned, reference is made to the substances mentioned at the beginning of the description which represent preferred other dye components. Particularly preferred other primary intermediates are 2,4,5,6-tetraaminopyrimidine, 4-hydroxy-2,5,6-triaminopyrimidine, dihydroxyaminopyridines, 1-(β-hydroxyethyl)-2,5-diaminobenzene, p-phenylenediamine, p-toluylenediamine, p-aminophenol, 3-methyl-4-aminophenol, 2,5-diaminophenoxyethanol, 2-hydroxymethyl-p-aminophenol and 2-aminomethyl-p-aminophenol. 4-Amino-2-(2-hydroxy-ethoxy)-phenol is another primary intermediate which may advantageously be combined with the primary intermediates according to the invention. These other primary and secondary intermediates are normally used in free form. However, in the case of compounds containing amino groups, it may be preferable to use them in salt form, particularly in the form of the hydrochlorides and sulfates.

The hair colorants according to the invention contain both the primary intermediates and the secondary intermediates in a quantity of, preferably, 0.005 to 20% by weight and, more preferably, 0.1 to 5% by weight, based on the oxidation colorant as a whole. The primary and secondary intermediates are generally used in a substantially equimolar ratio to one another. Although it has proved to be useful to employ the primary and secondary intermediates in an equimolar ratio, a certain excess of individual oxidation dye precursors is by no means a disadvantage, so that the primary and secondary intermediates may be present in a molar ratio of 1:0.5 to 1:2.

In one preferred embodiment, the hair colorants according to the invention contain typical substantive dyes in addition to the oxidation dye precursors for further modifying the color tones. The substantive dyes in question belong, for example, to the group of nitrophenylenediamines, nitroaminophenols, anthraquinones or indophenols such as, for example, the compounds known under the International names or commercial names of HC Yellow 2, HC Yellow 4, Basic Yellow 57, Disperse Orange 3, HC Red 3, HC Red BN, Basic Red 76, HC Blue 2, Nitroblau, Disperse Blue 3, Basic Blue 99, HC Violet 1, Disperse Violet 1, Disperse Violet 4, Disperse Black 9, Basic Brown 16, picramic acid and Rodol 9 R. These substantive dyes may be used in a quantity of 0.01 to 20% by weight, based on the oxidation hair colorant as a whole. According to the invention, 4-amino-2-nitrodiphenylamine-2-carboxylic acid, 6-nitro-1,2,3,4-tetrahydroquinoxaline, Rodol 9 R and HC Red BN are particularly preferred substantive dyes.

The oxidation dye precursors or the substantive dyes optionally present do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

To produce the colorants according to the invention, the oxidation dye precursors are incorporated in a suitable water-containing carrier. For coloring hair, such carriers are, for example, creams, emulsions, gels or even surfactant-containing foaming solutions, for example shampoos, foam aerosols or other formulations suitable for application to the hair.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide groups and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

- linear fatty acids containing 10 to 22 carbon atoms (soaps),
- ether carboxylic acids corresponding to the formula R—O—($CH_2$—$CH_2$O)$_x$-$CH_2$—COOH, in which R is a linear alkyl group containing 10 to 22 carbon atoms and x=0 or 1 to 16,
- acyl sarcosides containing 10 to 18 carbon atoms in the acyl group,
- acyl taurides containing 10 to 18 carbon atoms in the acyl group,
- acyl isethionates containing 10 to 18 carbon atoms in the acyl group,
- sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups,
- linear alkane sulfonates containing 12 to 18 carbon atoms,
- linear α-olefin sulfonates containing 12 to 18 carbon atoms,
- α-sulfofatty acid methyl esters of fatty acids containing 12 to 18 carbon atoms,
- alkyl sulfates and alkyl polyglycol ether sulfates corresponding to the formula R—O($CH_2$—$CH_2$O)$_x$—$OSO_3H$, in which R is a preferably linear alkyl group containing 10 to 18 carbon atoms and x=0 or 1 to 12,
- mixtures of surface-active hydroxysulfonates according to DE-A-37 25 030,
- sulfated hydroxyalkyl polyethylene and/or hydroxyalkylene propylene glycol ethers according to DE-A-37 23 354,
- sulfonates of unsaturated fatty acids containing 12 to 24 carbon atoms and 1 to 6 double bonds according to DE-A-39 26 344,
- esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —$COO^{(-)}$ or —$SO_3^{(-)}$ group in the molecule. Particularly suitable zwitterionic surfactants are the so called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

Nonionic surfactants contain, for example, a polyol group, a polyalkylene glycol ether group or a combination of polyol and polyglycol ether groups as the hydrophilic group. Examples of such compounds are

- products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group,
- $C_{12-22}$ fatty acid monoesters and diesters of products of the addition of 1 to 30 moles of ethylene oxide to glycerol,
- $C_{8-22}$ alkyl mono- and oligoglycosides and ethoxylated analogs thereof,
- products of the addition of 5 to 60 moles of ethylene oxide to castor oil and hydrogenated castor oil,
- products of the addition of ethylene oxide to sorbitan fatty acid esters,
- products of the addition of ethylene oxide to fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so called "esterquats", such as the dialkyl ammonium methosulfates and methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol, zwitterionic and amphoteric polymers such as, for example, acrylamidopropyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, carob bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose and maleic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solubilizers, such as ethanol, isopropanol, ethylene glycol, propylene glycol, glycerol and diethylene glycol, dyes for coloring the formulations, antidandruff agents, such as Piroctone Olamine and Zinc Omadine, other substances for adjusting the pH value, active substances, such as panthenol, pantothenic acid, allantoin, pyrrolidone carboxylic acids and salts thereof, plant extracts and vitamins, cholesterol, UV absorbers, consistency promoters, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlescers, such as ethylene glycol mono- and distearate, propellents, such as propanelbutane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

Basically, the color may be developed with atmospheric oxygen. However, a chemical oxidizing agent is preferably used, particularly when human hair is to be not only colored, but also lightened. Suitable oxidizing agents are persulfates, chlorites and, in particular, hydrogen peroxide or addition products thereof with urea, melamine and sodium borate. Oxidation may also be carried out with enzymes. In this case, the enzymes may be used to transfer atmospheric oxygen to the primary intermediate or to enhance the effect of oxidizing agents present in small quantities. One example of an enzymatic process is the procedure whereby the effect of small quantities (for example 1% and less, based on the formulation as a whole) of hydrogen peroxide is enhanced by peroxidases.

The preparation of the oxidizing agent is preferably mixed with the preparation of the oxidation dye precursors immediately before coloring of the hair. The ready-to-use hair coloring preparation formed should preferably have a pH value in the range from 6 to 10. In a particularly preferred embodiment, the hair colorant is used in a mildly alkaline medium. The application temperatures may be in the range from 15 to 40° C. After a contact time of about 30 minutes, the hair colorant is removed from the hair to be colored by rinsing. There is no need for the hair to be washed with a shampoo where a carrier of high surfactant content, for example a coloring shampoo, has been used.

The invention is illustrated by the following Examples.

EXAMPLES

1. Synthesis Examples 1.1. Synthesis of bis-(5-amino-2-hydroxyphenol)-methane

The following diazonium solution was prepared: 10.35 g (0.15 mote) of sodium nitrite in 125 ml of water were added at +5° C. to a solution consisting of 26 g (0.15 mole) of sulfanilic acid and 75 ml (0.15 mole) of 2 N sodium hydroxide. After the solution had been recooled to +5° C., 131 ml (0.38 mole) of 10% hydrochloric acid were added dropwise over a period of 30 minutes. This solution was then added to an ice-cooled solution consisting of 10.0 g (0.05 mole) of bis-(2-hydroxyphenyl)-methane in 120 ml of 10% sodium hydroxide. After the addition, the solution was stirred for 1.5 hours at 20° C. 69 g (0.4 mole) of sodium dithionite were then added to this solution over a period of 2 minutes. After 20 minutes at 75° C., the product was filtered under suction and washed with water. The yield amounted to 54% of the theoretical. The product had a melting point of 198.0° C.

1.2. Synthesis of 3-hydroxy-6-aminoallyloxybenzene

The synthesis corresponded to Example 1.1. except that 3-hydroxy-1-allyloxybenzene prepared by a method known from the literature (J. Am. Chem. Soc. 52, 1702 (1930)) was used instead of bis-(2-hydroxyphenyl)-methane as the starting product. The product accumulated in the form of light brown crystals melting at 110 to 114° C.

1.3. 2-Hydroxy-5-aminoallyloxybenzene

The synthesis corresponded to Example 1.2., except that 2-hydroxy-1-allyloxybenzene prepared by a method known from the literature (J. Am. Chem. Soc. 52, 1702 (1930)) was used as the starting material. The product accumulated in the form of light brown crystals melting at 122° C.

1.4. 5-Amino-2-hydroxycinnamic acid (HCl salt)

The synthesis corresponded to Example 1.1. using o-hydroxycinnamic acid as the starting material. The product had a melting point (with decomposition) of about 260° C.

1.5. Bis-[2-(2-hydroxy-5-aminophenoxy)-ethyl]-ether

In a 600 ml glass beaker, 13.9 g (0.08 mole) of sulfanilic acid were dissolved in 41 ml of 10% sodium hydroxide solution and a solution of 5.7 g (0.08 mole) of sodium nitrite in 30 ml of water was added to the resulting solution. After the mixture had been cooled to 0–5° C., 72 ml of 10% hydrochloric acid were added dropwise over a period of 45 minutes. This cold diazonium solution was then added dropwise over a period of 30 minutes at 0–5° C. to a solution of 11.8 g (0.04 mole) of bis-([-2-(2-hydroxyphenoxy)-ethyl]-ether (prepared in accordance with J. Am. Chem. Soc. (1977), 2568) in 66 ml of 10% sodium hydroxide. After stirring for another 1.5 hours at 15° C., 38.3 g (0.22 mole) of sodium dithionite were added. The mixture was then heated for 20 minutes to 75° C., the product precipitating. After cooling, the product was filtered off under suction, washed with water and dried in vacuo at 70° C. The product had a melting point of 215° C. (with decomposition).

1.6. 1,8-Bis-[2-hydroxy-5-aminophenoxy]-3,6-dioxaoctane

The synthesis corresponded to Example 1.5., except that 1,8-bis-(2-hydroxyphenoxy)-3,6-dioxaoctane was used as the starting material. This compound had been prepared in accordance with Ann. (1978), 1594. The product had a melting point of 144.5° C. (with decomposition).

1.7. 1.3-Bis-(2-hydroxy-5-aminophenoxy)-propane

The synthesis corresponded to Example 1.5., except that 1,3-bis-(2-hydroxyphenoxy)-propane was used as the starting material. This compound had been prepared in accordance with J. Org. Chem. 48, 4867 (1983). The product had a melting point of 150° C. (with decomposition).

1.8. 1,3-Bis-(2-hydroxy-5-aminophenoxy)-propan-2-ol

The synthesis corresponded to Example 1.5., except that 1,3-bis-(2-hydroxyphenoxy)-propan-2-ol was used as the starting material. This compound had been prepared in accordance with J. Chem. Soc., Perkin Trans I (1978), 451. The product had a melting point of 215° C. (with decomposition).

2. Coloring

A cream base with the following composition was initially prepared [all quantities in g, unless otherwise indicated]:

tallow fatty alcohol 17.0

Lorol®techn.[1] 4.0

Texapon®N 28[2] 40.0

Dehyton®K[3] 25.0

Eumulgin®B 2[4] 1.5 distilled water 12.5

[1] $C_{12-18}$ fatty alcohol (HENKEL)
[2] Sodium lauryl ether sulfate (ca. 28% active substance; CTFA name: Sodium Laureth Sulfate) (HENKEL)
[3] Fatty acid amide derivative of betaine structure corresponding to the formula: $R\text{-CONH}(CH_2)_3N^+(CH_3)_2CH_2COO^-$ (ca. 30% active substance; CTFA name: Cocoamidopropyl Betaine) (HENKEL)
[4] Cetylstearyl alcohol containing ca. 20 moles EO (CTFA name: Ceteareth-20) (HENKEL)

The following hair coloring cream emulsion was then prepared on the basis of this cream:

cream base 50.0 primary intermediate 7.5 mmoles secondary intermediate 7.5 mmoles $Na_2SO_3$ (inhibitor) 1.0

$(NH_4)_2SO_4$ 1.0 conc. ammonium solution to pH 10 water to 100

The ingredients were mixed together in the above order. After addition of the oxidation dye precursors and the inhibitor, the pH of the emulsion was first adjusted to a value of 10 with concentrated ammonia solution, after which the emulsion was made to 100 g with water.

The color was oxidatively developed with 3% hydrogen peroxide solution as the oxidizing solution. To this end, 50 g of hydrogen peroxide solution (3%) were added to and mixed with 100 g of the emulsion.

The coloring cream was applied to ca. 5 cm long tresses of standardized, 90% grey but not especially pretreated human hair and left thereon for 30 minutes at 32° C. On completion of the coloring process, the hair was rinsed, washed with a standard shampoo and then dried.

The following primary and secondary intermediates were used in the coloring emulsions:

Primary Intermediates bis-(5-amino-2-hydroxyphenyl)-methane (P1),
3-hydroxy-6-aminoallyloxybenzene (P2),
2-hydroxy-5-aminoallyloxybenzene (P3),
5-amino-2-hydroxycinnamic acid (P4),
bis-[2-(2-hydroxy-5-aminophenoxy)-ethyl]-ether (P5),
1,8-bis-(2-hydroxy-5-aminophenoxy)-3,6-dioxaoctane (P6),
1,3-bis-(2-hydroxy-5-aminophenoxy)-propane (P7),
1,3-bis-(2-hydroxy-5-aminophenoxy)-propan-2-ol (P8) and
4-amino-2-(2-hydroxyethoxy)-phenol (P9)

Secondary Intermediates 2-methyl-5-aminophenol (S1),
1-naphthol (S2),
2-chloro-6-methyl-3-aminophenol (S3),
1,3-bis-(2,4-diaminophenoxy)-propane (S4),
2-methyl-5-(2-hydroxyethylamino)-phenol (S5),
resorcinol (S6),
1,5-dihydroxynaphthalene (S7).

The following colors were obtained:

| Primary intermediate | Secondary intermediate | Color of the dyed hair |
|---|---|---|
| P1 | S1 | Red-brown |
| P1 | S2 | Violet-brown |
| P1 | S3 | Pompeian red |
| P1 | S4 | Dark magenta |
| P1 | S5 | Terracotta |
| P2 | S2 | Dark magenta |
| P2 | S3 | Violet-brown |
| P2 | S6 | Dark turquoise |
| P3 | S1 | Grey-red |
| P3 | S7 | Violet-brown |
| P4 | S1 | Red-yellow |
| P4 | S3 | Red-brown |
| P4 | S7 | Grey-red |
| P5 | S3 | Leather brown |
| P5 | S1 | Grey-red |
| P6 | S1 | Caramel-brown |
| P6 | S3 | Red-brown |
| P7 | S3 | Red-brown |
| P7 | S7 | Deer brown |
| P8 | S2 | Violet-brown |
| P8 | S7 | Violet-brown |
| P9 | S1 | Red-brown |
| P9 | S2 | Violet-brown |
| P9 | S3 | Violet-brown |
| P9 | S4 | Dark brown |
| P9 | S5 | Red-brown |
| P9 | S6 | Gold |

What is claimed is:

1. A method of coloring a keratinous fiber comprising applying to said fiber as a primary intermediate an effective amount of a compound of formula (I) or a water soluble-salt thereof:

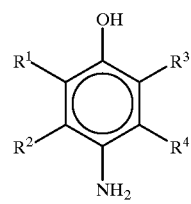

wherein one of $R^1$ and $R^2$ is hydrogen while the other is hydrogen, chlorine or fluorine, and wherein one of $R^3$ and $R^4$ is hydrogen, $C_{1-4}$ alkyl, $C_{1-4}$ alkoxy, $C_{1-4}$ hydroxyalkyl, or a halogen while the other is —O—CH$_2$—CH=CH$_2$, CH=CH—COOX where X is hydrogen or a physiologically compatible inorganic or organic cation, or for $R^3$ only a group of the formula:

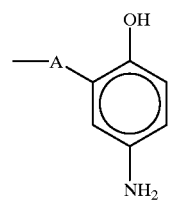

or for $R^4$ only a group of the formula:

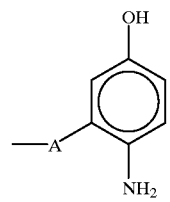

wherein —A— is —(CH$_2$)$_x$— and x=1-4, —O—(CH$_2$)$_y$—O— and y=1-4, —O—(C$_n$H$_{2n-z}$(OH)$_z$)—O— and n=1-10 and z=1 or, where n is 3 or >3, z=2, —O—(C$_2$H$_4$—O)$_u$— and u=1-4, or —O—(C$_3$H$_6$—O)$_v$— and v=1-4, and oxidizing said primary intermediate to color said fiber.

2. The method according to claim 1, wherein $R^1$ and $R^2$ are hydrogen.

3. The method according to claim 1, wherein $R^3$ or $R^4$ is hydrogen.

4. The method according to claim 1, wherein X is hydrogen.

5. The method according to claim 1, wherein n=1 to 6 and z=1.

6. The method according to claim 5, wherein n=1 to 3.

7. The method according to claim 1 comprising contacting said fiber with at least one other primary intermediate.

8. The method according to claim 7, wherein the other primary intermediate is selected from the group consisting of 2,4,5,6-tetraaminopyrimidine, 4-hydroxy-2,5,6-triaminopyrimidine, 1-(β-hydroxyethyl)-2,5-diaminobenzene, p-phenylenediamine, p-toluylenediamine, p-aminophenol, 3-methyl-p-aminophenol, and 2-aminomethyl-p-aminophenol.

9. A method of coloring a keratinous fiber, comprising contacting said fiber with an effective amount of an oxidation colorant comprising 0.005% to 20% by weight of a primary intermediate and 0.005% to 20% by weight of a secondary intermediate, wherein the primary intermediate comprises a compound of the formula (I) or a water soluble-salt thereof:

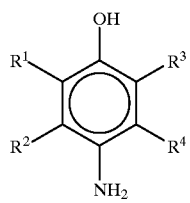

(I)

wherein one of $R^1$ and $R^2$ is hydrogen while the other is hydrogen, chlorine or fluorine, and wherein one of $R^3$ and $R^4$ is hydrogen, $C_{1-4}$ alkyl, $C_{1-4}$ hydroxyalkyl, or a halogen while the other is —O—$CH_2$—CH=$CH_2$, —CH=CH—COOX where X is hydrogen or a physiologically compatible inorganic or organic cation, or for $R^3$ only a group of the formula:

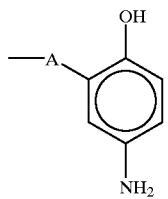

or for $R^4$ only a group of the formula:

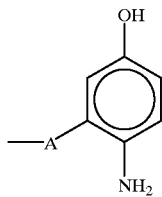

wherein —A— is —$(CH_2)_x$— and x=1–4, —O—$(CH_2)_y$—O— and y=1–4, —O—$(C_nH_{2n-z}(OH)_z)$—O— and n=1–10 and z=1 or, where n is 3 or >3, z=2, —O—$(C_2H_4$—O$)_u$— and u=2–4, or —O—$(C_3H_6$—O$)_v$— and v=1–4, and oxidizing said primary intermediate to color said fiber.

10. The method according to claim 9, wherein the oxidation colorant comprises 0.1% to 5% by weight primary intermediate and 0.1% to 5% by weight secondary intermediate.

11. The method according to claim 9, wherein the oxidation colorant further comprises a substantive dye.

12. The method according to claim 1, wherein $R^1$ and $R^2$ are hydrogen, $R^3$ or $R^4$ is hydrogen, X is hydrogen, n=1 to 6, and z=1.

13. The method according to claim 1, wherein $R^3$ or $R^4$ is $C_{1-4}$ hydroxyalkyl having a terminal hydroxy group.

14. The method according to claim 9, wherein $R^3$ or $R^4$ is $C_{1-4}$ hydroxyalkyl having a terminal hydroxy group.

15. A composition for coloring keratin fibers comprising:
  (a) a coloring effective amount of at least one primary intermediate of formula (1) or a water soluble-salt thereof

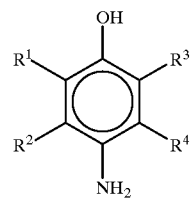

(I)

wherein one of $R^1$ and $R^2$ is hydrogen while the other is hydrogen, chlorine or fluorine, and wherein one of $R^3$ and $R^4$ is hydrogen, $C_{1-4}$ alkyl, $C_{1-4}$ alkoxy, $C_{1-4}$ hydroxyalkyl, or a halogen while the other is —O—$CH_2$—CH=$CH_2$, —CH=CH—COOX where X is hydrogen or a physiologically compatible inorganic or organic cation, or for $R^3$ only a group of the formula:

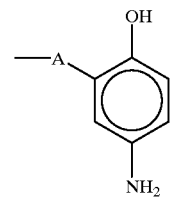

or for $R^4$ only a group of the formula:

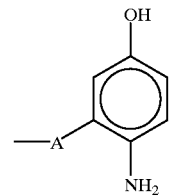

wherein —A— is —$(CH_2)_x$— and x=1–4, —O—$(CH_2)_y$—O— and y=1–4, —O—$(C_nH_{2n-z}(OH)_z)$—O— and n=1–10 and z=1 or, where n is 3 or >3, z=2, —O—$(C_2H_4$—O$)_u$— and u=2–4, or —O—$(C_3H_6$—O$)_v$— and v=1–4; and
  (b) at least one second primary intermediate or at least one secondary intermediate, or combinations thereof in an effective amount for coloring keratin fibers.

16. The composition according to claim 15, wherein $R^1$ and $R^2$ are hydrogen, and $R^3$ or $R^4$ is hydrogen.

17. The composition according to claim 15, wherein X is hydrogen.

18. The composition according to claim 15, wherein n=1 to 6 and z=1.

19. The composition according to claim 15, wherein the composition comprises from 0.005% to 20% by weight of the primary intermediates and from 0.005% to 20% by weight of the secondary intermediate.

20. The composition according to claim 19, wherein the second primary intermediate is selected from the group consisting of 2,4,5,6-tetraaminopyrimidine, 4-hydroxy-2,5,6-triaminopyrimidine, 1-(β-hydroxyethyl)-2,5-diaminobenzene, p-phenylenediamine, p-toluylenediamine, p-aminophenol, 3-methyl-p-aminophenol, and 2-aminomethyl-p-aminophenol.

21. The composition according to claim 15, wherein the composition further comprises a substantive dye.

22. The composition according to claim 15, wherein $R^3$ or $R^4$ is $C_{1-4}$ hydroxyalkyl having a terminal hydroxy group.

23. The method of claim 1, wherein $R^3$ is a group of the formula:

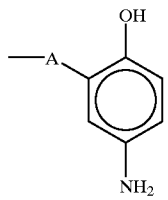

or $R^4$ is a group of the formula:

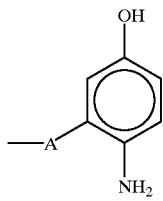

wherein —A— is —$(CH_2)_x$— and x=1–4, —O—$(CH_2)_y$—O— and y=1–4, —O—$(C_nH_{2n-z}(OH)_2)$—O— and n=1–10 and z=1 or, where n is 3 or >3, z=2, —O—$(C_2H_4$—$O)_u$— and u=1–4, or —O—$(C_3H_6$—$O)_v$— and v=1–4.

24. The method of claim 23, wherein —A— is —$(CH_2)_x$— and x=1–4.

25. The method of claim 24, wherein the compound of formula (I) is bis-(5-amino-2-hydroxyphenyl)-methane.

26. The method of claim 9, wherein $R^3$ is a group of the formula:

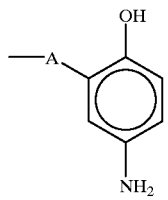

or $R^4$ is a group of the formula:

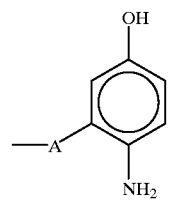

wherein —A— is —$(CH_2)_x$— and x=1–4, —O—$(CH_2)_y$—O— and y=1–4, —O—$(C_nH_{2n-z}(OH)_2)$—O— and n=1–10 and z=1 or, where n is 3 or >3, z=2, —O—$(C_2H_4$—$O)_u$— and u=1–4, or —O—$(C_3H_6$—$O)_v$— and v=1–4.

27. The method of claim 26, wherein —A— is —$(CH_2)_x$— and x=1–4.

28. The method of claim 27, wherein the compound of formula (1) is bis-(5-amino-2-hydroxyphenyl)-methane.

29. The composition of claim 15, wherein $R^3$ is a group of the formula:

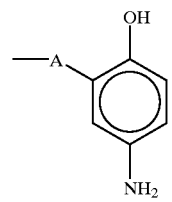

or $R^4$ is a group of the formula:

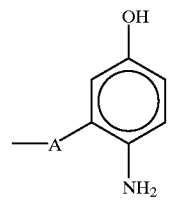

wherein —A— is —$(CH_2)_x$— and x=1–4, —O—$(CH_2)_y$—O— and y=1–4, —O—$(C_nH_{2n-z}(OH)_2)$—O— and n=1–10 and z=1 or, where n is 3 or >3, z=2, —O—$(C_2H_4$—$O)_u$— and u=1–4, or —O—$(C_3H_6$—$O)_v$— and v=1–4.

30. The composition of claim 29, wherein —A— is—$(CH_2)_x$— and x=1–4.

31. The composition of claim 30, wherein the primary intermediate of formula (1) is bis-(5-amino-2-hydroxyphenyl)-methane.

* * * * *

UNITED STATES PATENT AND TRADEMARK OFFICE
CERTIFICATE OF CORRECTION

PATENT NO. : 6,635,241 B1
DATED : October 21, 2003
INVENTOR(S) : Rose et al.

It is certified that error appears in the above-identified patent and that said Letters Patent is hereby corrected as shown below:

Column 12,
Line 16, delete "CH=CH-COOX", and insert therefore -- -CH=CH-COOX --.

Column 13,
Line 16, delete "alkyl,", insert -- $C_{1-4}$ alkoxy, --.
Line 46, delete "u-2-4", insert therefore -- u=2-4 --.

Column 14,
Line 41, delete "-O-$(C_nH_{2n-z}(OH)_2)$-O-" and insert therefore -- -O-$(C_nH_{2n-z}(OH)_z)$-O- --.

Column 15,
Line 28, delete "-O-$(C_nH_{2n-z}(OH)_2)$-O-" and insert therefore -- -O-$(C_nH_{2n-z}(OH)_z)$-O- --.

Column 16,
Lines 13 and 43, delete "-O-$(C_nH_{2n-z}(OH)_2)$-O-" and insert therefore
-- -O-$(C_nH_{2n-z}(OH)_z)$-O- --.

Signed and Sealed this

Twenty-sixth Day of July, 2005

JON W. DUDAS
*Director of the United States Patent and Trademark Office*